United States Patent [19]
Infante Martinez-Pardo et al.

[11] Patent Number: 5,994,406
[45] Date of Patent: Nov. 30, 1999

[54] GEMINAL CATIONIC SURFACTANTS OF THE TYPE Nα Nω BIS (Nα-ACYL-ARGININ) α,ω DIAMINO ALKYL DICHLOROHYDRATES AS ANTIMICROBIAL AGENTS

[75] Inventors: Maria Rosa Infante Martinez-Pardo; Lourdes Perez Muńoz, both of Barcelona, Spain

[73] Assignee: Consejo Superior Investigaciones Cientificas, Madrid, Spain

[21] Appl. No.: 08/718,533

[22] PCT Filed: Feb. 8, 1996

[86] PCT No.: PCT/ES96/00026

§ 371 Date: Dec. 13, 1996

§ 102(e) Date: Dec. 13, 1996

[87] PCT Pub. No.: WO96/24528

PCT Pub. Date: Aug. 15, 1996

[30] Foreign Application Priority Data

Feb. 9, 1995 [ES] Spain ........................... 9500265

[51] Int. Cl.[6] .................. A61K 31/16; C07C 233/04; A01N 37/18
[52] U.S. Cl. .................. 514/616; 424/78.03; 424/405; 510/131; 510/382; 510/383; 514/19; 514/20; 564/153; 564/159
[58] Field of Search ..................... 564/153, 159; 514/616, 19, 20; 510/131, 382, 383; 424/405, 78.03; 252/FOR 131, FOR 196

[56] References Cited

FOREIGN PATENT DOCUMENTS 551863  12/1986  Spain .

OTHER PUBLICATIONS

Infante et.al,JAOCS, vol. 69, No. 7, pp. 647–652, 1992.

*Primary Examiner*—Shailendra Kumar
*Attorney, Agent, or Firm*—Klauber & Jackson

[57] ABSTRACT

Surfactants having general formula (II)

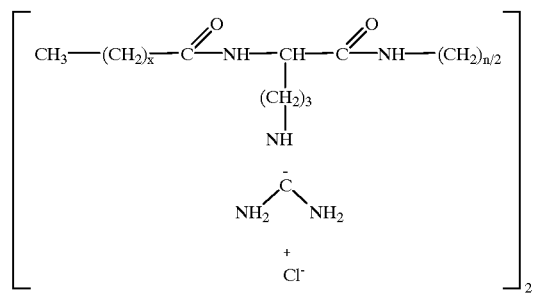

wherein X=8–14; n=2–8. The process for obtaining such surfactants comprises the following steps;

a) producing nitroarginin; b) producing $N_\alpha$-acyl-nitroarginin c) producing $N_\alpha$ $N_\omega$ bis ($N_\alpha$acyl-arginin) $_{\alpha,\omega}$ diaminoalkylamide dichlorohydrate. Said surfactants are antimicrobial agents which can be applied in cosmetics, pharmacy and food industry.

7 Claims, No Drawings

GEMINAL CATIONIC SURFACTANTS OF THE TYPE Nα Nω BIS (Nα-ACYL-ARGININ) α,ω DIAMINO ALKYL DICHLOROHYDRATES AS ANTIMICROBIAL AGENTS

INTRODUCTION

As is well known, the surfactants are organic molecules which contain two functional groups with opposed characteristics. A conventional surfactant contains an absorbent group (water soluble) and a hydrophobic group (insoluble in water) both in the same molecule. This structure is known as amphiphilic structure.

Though at present it may be considered that the industry has available the suitable surfactants, the ecological demands, currently force research and development of new alternatives which protect and improve the environment and quality of life.

Numerous structural modifications have been made to improve the biocompatibility of these compounds, either parting from natural raw materials such as aminoacids and/or sugars, or by increasing the hydrophobic interaction of these compounds in an intent to potentiate their surface activity and in consequence their efficiency.

Among the numerous structural modifications described in literature, the following deserve our attention; those which give arise to dimeric or geminal surfactants characterized by containing in the same molecule, two or more hydrophobic chains together with various ionic groups. It is described that such structures reinforce the intra or inter-molecular hydrophobe interactions, with the consequent result of different highly efficient surfactants and in some cases with excellent aqueous solubility properties.

These materials have demonstrate that they have unforeseeable physico-chemical properties (i.e. extremely low CMCs and great absorbant effectivity on the surfactants) which consequently contributes to optimize the environmental aspects of the surfactants.

Among the ionic geminal surfactants, the bicationic quaternary ammonium salts must be highlighted, which are also known as bis-QUATS, for their excellent antimicrobial properties, especially versus Gram negative bacteria, when compared with the classical mono-QUATS. However, since they are quaternary ammonium salts, it is known that they are resistant to biodegradation and in consequence their ecological acceptability is questioned.

The present invention pretends to overcome this aspect by dimerizing ecologically acceptable cationic surfactants, such as the monocatenaries y derivatives of the $N^{\alpha}$-acyl-arginin. The new structure shall present the double advantage of being efficient as regards surface (due to its geminal structure) and biodegradable (since it is an aminoacid derivate).

PRIOR ART TO THE INVENTION

Though the literature includes a great variety of descriptions on antimicrobial surfactants with geminal bicationic structures, the compounds which are the object of the present patent are a novelty and no similar reference is described in the same. The novelty of the present invention is the result of the combination of one same molecule with two residues of $N^{\alpha}$-acyl-arginin in one geminal mimetic structure to the bis-QUATS.

The synthesis and development of the monocatenary derivatives of the $N_{\alpha}$-acylarginin have been carried out by our team after many years of study, which has originated a great number of results and publications (Spanish Patent 512.643; M. R. Infante, J. Molinero and P. Erra, JAOCS, Vol.69, N97, 1992; J. Molinero, M. R. Julia, P. Erra, M. Robert and M. R. Infante, JAOCS, Vol. 65, No. 6 1988; C. Solans, M. A. Pes; N. Azemar and M. R. Infante, Progr. Colloid Polym Sci81.pp 144–150, 1990).

On the other hand, since the 50's, numerous bifunctional structures are known, of the type bis-QUATS ((A) C. A. Bunton, L. Robinson, J. Schaak and M. F. Stam, J. Org. Chem., 1971, 36, 2346; (b) R. Zana, M. Benrraou and R. Rueff, Langmuir, 1991,. 7.1072; (c) F. Dvinski, L. Lacko and T. Imam, J. Colioid Interface Sci., 1991, 143,336; (d) R. Zana and Y. Talmon, Nature, 1993,. 362.228; (f) H. C. Parreira, E. R. Lukenbach and M. K. Lindemann, J. Am. Oil chem. SOC., 1979, 56,1015) the formula of which could be the diagram according to I.

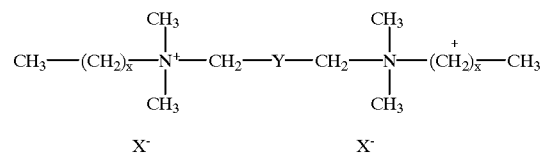

wherein X: 0–17
Y: $(CH_2)_n$, $NCH_3$, O, S
X: Br, Cl ...

These compounds contain per molecule two hydrophobic chains, two groups of quaternary ammonium and one spacer chain, Y, of alkylic or etheroatomic nature.

The growing interest for these bifunctional surfactant agents is a consequence of their unusual physio-chemical properties (high absorption affectivity, a rich basic polymorphism and a great capacity of selfaddition) which gives place to their interesting applications in biological researches.((A) J. H. Fuhrhop and U. Uman, J. Am. Chem. Soc., 1984,106,4643; (b) C. Tanford, the Hydrophobic Effect, Wiley, N.Y.;1980; (C) M. Lissel, D. Feldman, M. Nir and M. Rabinovitz, Tetrahedron Lett., 1989, 30, 1683). In this sense, our group has recently patented new surfactants bis-QUATS, characterized by having in the spacer chain, a disulphur bridge, (Spanish Patent 9200443), to be applied mainly on keratinic substrates.

DESCRIPTION OF THE INVENTION

The present invention refers in particular to a new family of dimeric surfactants derived from arginin of cationic nature, the structural formula of which is indicated in II

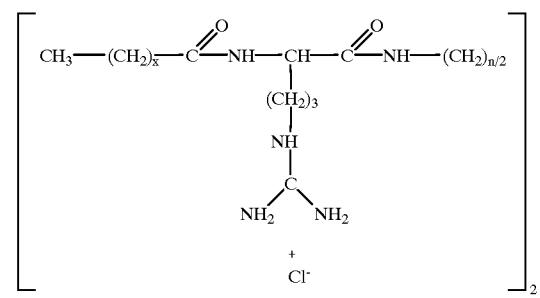

wherein x = 8–14; n = 2–8

These compounds simultaneously group together in the same molecule two residues of $N^{\alpha}$-acyl-arginin linked through an alkylic spacer chain. They have been designed in such a manner that the length of the spacer contributes to reinforce the inter or intramolecular hydrophobic interactions, giving place in consequence to a different behaviour in the absorption properties and the molecular aggregation, and additionally, since it is cationic, to a different antimicrobial behaviour.

Structurally speaking, they are symmetric compounds and contain in the same molecule, two saturated or unsaturated hydrocarboned chains of 6 to 20 atoms of carbon as hydrophobe part, linked to various rests of the arginin aminoacid, which are interlinked through a spacer chain of the alkyldiamino type. The residue of $N_\alpha$acyl arginin acts as source both of the hydrophobe part and of the cationic group. Each one of the functional groups which constitutes the molecule (fatty acid, aminoacid, alkyldiamine) are interlinked through amide links which assures the stability of the molecule to values of pH: 3–9 at the same time as the molecule is more biodegradable in comparison with the already known bisQUATS. The hydrolysis products which are to be expected to be fatty acid, arginin and a diamine, none of which is hazardous, both from the biological and from the ecological point of view.

The synthesis of these compounds has taken place in four phases:
  a) Formation of nitroarginin, using start from aminoacid Larg, D-arg or DL-arg and as protector of the guanidine group of the arginin, the nitro group.
  b) Formation of $N_\alpha$-acyl-nitroarginin parting from the nitroarginin and fatty acid, using lineal oil acid chlorides, of 8 to 18 atoms as acylants of the nitroarginin in a hydroalcoholic medium.
  c) Formation of $N_\alpha,N_\omega$, bis ($N_\alpha$-acyl-nitroarginin) $\alpha,\omega$ diaminoalkylamide starting from $N_\alpha$-acyl-nitroarginin and diaminoakyl, using condensation agents such as BOP (hexafluorphosphate of benzotriazo N-oxytris-dimethylamino-phosphoni) or DCCD (Dicycloxylcarbodimide).
  d) Formation of $N_\alpha N_\omega (N_\alpha$-acylarginin) $\alpha,\omega$ diaminoalkylamide dichlorhydrate by means of a catalytic hydrogenation, in PD/C (palladium/carbon) and methanol-formic acid in a proportion comprised between 30–50% of formic acid, of $N_\alpha N_\omega$ $_{bis\ (N\alpha\text{-}}$ acylnitroarginin) $\alpha,\omega$ diaminoalkyl.

The present invention refers to new geminal bicationic surfactant compounds derived from the arginin aminoacid specifically designed to act as efficient surface agents and in consequence as powerful antimicrobial agents. The variations of the activity shall be a function of the length of the fatty chain, as well as of the length of the spacer chain.

The invention refers to molecules with structural characteristics as follows:

To possess in the same molecule two fatty hydrocarbonated chains, two cationic groups of the guanidine type provided by the two lateral residues of the arginin aminoacid and a spacer chain of the alkyl type of different length. These molecules, since they are geminal, will show a strong synergy in their hydrophobic interaction, being cationic they shall have a specific substantivity by the microorganisms acting as effective antimicrobial agents and by being derivatives of the $N_\alpha$-acyl-arginin shall be biodegradable compounds and compatible with the environment.

The compounds have been prepared with a 99% purity using for this a synthetic route systematically confronted parting from raw material and non competitive cost intermediates.

The preparation of the final products has taken place during four phases such as has been indicated in the general diagram 1:

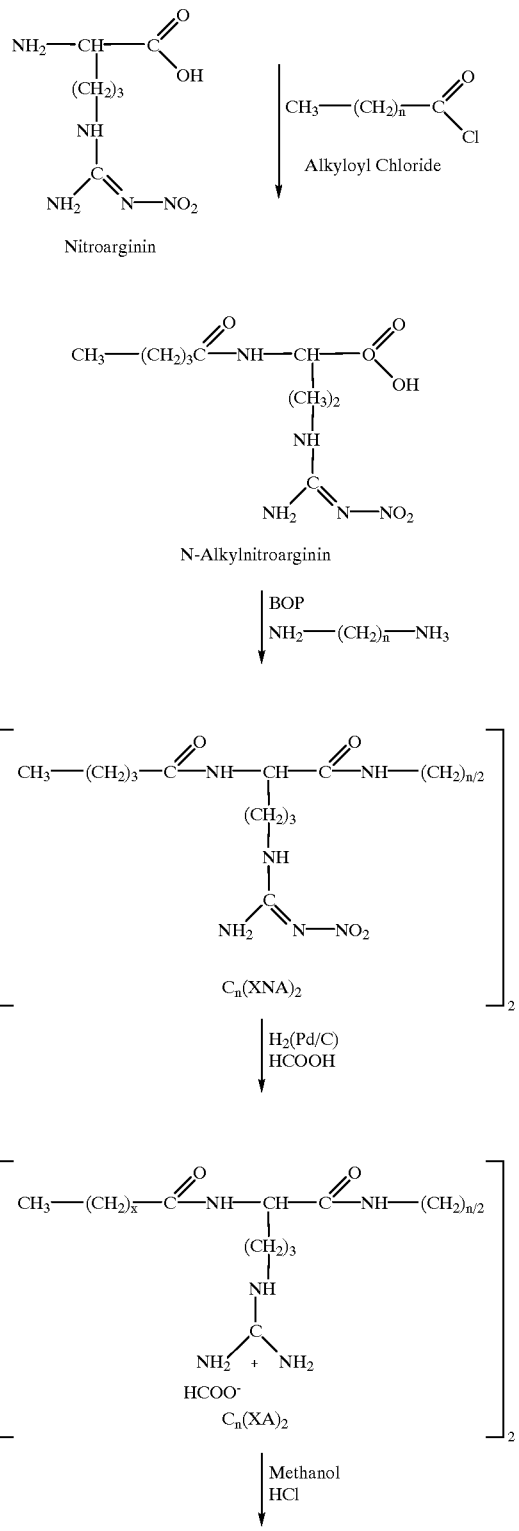

-continued

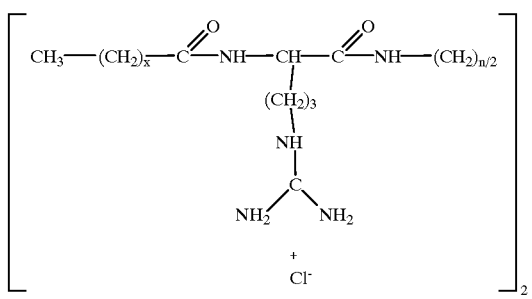

wherein x: 8–14
n: 2–8

The preparation of the $N_\alpha$-acyl-nitroarginin takes place during the two first stages by means of already known procedures. The compound formed by means of the simultaneous condensation of the alkylic diamine with two molecules of the $N_\alpha$-acyl-nitroarginin is a novelty, though it takes place using the classic condensation agent BOP.

The obtention of the final products is achieved during the last stage by catalytic hydrogenation in Pd/C and formic.

All these reactions take place at low temperatures and employing solvents such as : $H_2O$, EtOH, $CL_2$ CH, and formic/MeOH.

Under these conditions, the products are isolated without difficulty, keeping them stable through-out all the process.

The purification of the intermediate and final products is conducted by liquid/liquid, liquid/solid, extractions, crystallization and preparative HPLC.

The synthesized compounds are antimicrobial cationic surfactants of high purity, soluble in water and stable in an aqueous medium at pH values comprised between 3 and 9 and at temperatures of up to 70° C. Their appearance is of very hygroscopic white solids.

As regards their corresponding monomers (Pat. No. 2512.643), the compounds of the present invention present great efficiency for being absorbed in the aqueous surfaces, great facility for forming micelles and show a substantial improvement in the antimicrobial activity specially versus Gram positive bacteria.

The compounds are prepared as has been previously indicated, in four steps:

a) Conducted by means of the following reaction: disolve hydrochloride of L-arginin in concentrated sulphuric acid, in the proportion of 50% volume, eliminating the hydrochloric acid formed, into air; to this solution is added a quantity of pulverized ammonium nitrate and left to react at least 15 minutes at room temperature and after eliminating the gas which has formed, pour the mixture on ground ice and cool at 0° C. the solution is brought to 6.8 pH by the addition of concentrated ammonium and kept at a temperature of 0° C. until the total precipitation of the product, approximately 48 hours; the thus formed precipitate is filtered and crystallized with hot water.

b) A solution is prepared in the range of 0.10–0.30 mol of nitroarginin and Na(OH) in an aqueous solution of 20 to 30% acetone; next add slowly an equimolecular quantity of fatty acid chloride keeping the pH comprised between 11 and 13 by means of the addition of Na (OH). The mixture is maintained, agitating during various hours, and HCl is added up to acid pH, a white precipitate appearing, which is filtered, washed with water and ether and finally, crystallized in ethanol-ether.

c) A solution is prepared of 0.30–0.50 mol of $N_\alpha$-acyl-nitroarginin and an excess of tertiary organic base (triethylamine or N-methylmorpholin) in chloroform or else dimethylformamide. To this mixture is added the condensing agent BOP in a concentration comprised between 0.30–0.50 mol and the alkyldiamine in a concentration comprised between 0.15 and 0.25 mole. The mixture of the reaction is maintained under agitation between 15–30 hours at a temperature comprised between 10 and 25° C., subsequently adding ether, a precipitate appearing which is washed various times with ether.

d) It is conducted by means of the deprotection of the nitro group for obtaining the dimers $N^\alpha$-acyl-nitroarginin by a catalytic hydrogenation in a medium which contains PD/C and methanol-formic acid in a proportion comprised between 30–50% in formic acid to a pressure of at least 50 atm, room temperature and in a maximum time of 24 hours.

EXAMPLE

Synthesis of $N_\alpha$, $N_\omega$, Bis ($N_\alpha$-Decanoilarginin) α, ω-Diaminobuthylamide[$C_4(KA)_2$]

Equimolecular quantities of nitroarginin (0.0685 m) and Na(OH) are dissolved in 290 ml of an aqueous acetone solution, 34% (v/v). Next, the same number of decaloil chloride moles (0.0685) were added, drop by drop and very slowly, controlling that the pH was maintained comprised between 11 and 13 by means of the addition of Na(OH). The reaction mixture was maintained under agitation during two hours, adding after this time had elapsed HCl up to pH=1, when a white precipitate appeared. This solid was filtered and washed with water up to neutral pH, subsequently washing with ether and crystalize in ethanol-ether, obtaining the pure NaDecanoilnitroarginin.

Next, 0.021 moles of $N_\alpha$-Decanoilnitroarginin are dissolved in 50 ml of chloroform and 0.050 moles of triethylamine. To this solution is added 0.010 moles of Butyldiamine and 0.021 moles of BOP (hexafluorophosphate of benzotriazol N—oxo—tris(dimethylamine)phosphonium) The thus obtained reaction mixture is maintained under agitation during 24 hours at room temperature. The next day, ether is added to this mixture and a yellow and viscous precipitate appears, it is filtered and the residue is dissolved in methanol resting for 24 hours at a temperature of 4° C. After this time has elapsed in the methanol, we obtain a solid residue which is filtered to the air and washed various times in a sosiher with ether.

Depending on the purity desired, the thus obtained mixture is dissolved in formic acid and purified by means of successive crystallizations in MeOH or else by applying the HPLC preparation technique.

Once pure, the product, $C_4(KNA)_2$, is subjected to a catalytic hydrogenation with PD/C in a formic acid medium and at a pressure of 600 psi during 24 hours. The thus resultant mixture is filtered, the solvent eliminated, and it is disolved in water and lyophilized. The solid obtained is crystalized in MeOH(ClH)/ether, thus obtaining the dichlorohydrated $C_4(KA)_2$.

Characteristics of the product: $C_4(KA)_2$

Molecular weight: 746

CCF ($SIO_2$ Butanol/Acetic/Water 4.2:6:2.5) Rf: 0,64

IR (KB r): 3300 $cm^{-1}$ (NH): 2923 $cm^{-1}$ ($\underline{CH_2}$): 1638, 1621 $cm^{-1}$ ($\underline{CO}$-N amide I), 1546 $cm^{-1}$ (N—C=O, amide II):

$^1$H-NMR (200 MHz, δ): 0, 84 ppm (t, 6H, 2CH$_3$); 1,2–1,7 ppm (m,4OH,CH$_2$); 2,1 ppm (t,4H, 2CH$_2$); 1,3 ppm (m,8H, 4CH$_2$—NH); 4,2 ppm (m,2H, 2CH); 7,5–8,5 ppm (m,14H, 6NH, 4NH$_2$).

$^{13}$C-NMR (50 MHz, δ); 13,93 ppm (CH$_3$); 22–40 ppm (CH$_2$;-51,90 ppm (CH); 157,42 ppm (C, guanidino group) ; 171,523 ppm (1 HN—C=O, amide) 172,28 ppm (1HN—C=O, amide)

The main properties of the surface activity in aqueous solution at 25° C. which define the practical interest of a surfactant; surface stress to the critical micellar concentration (γ) and critical micellar concentration (CMC) have been determined according to conventional methods. Likewise, the antimicrobial activity has been evaluated based on the inhibiting minimum concentration values (MIC) expressed in μg/mL following the most common methodologies. Table 1 indicates the values of λ, CMC and MIC for two dimers of the same homologous series; C$_4$(KA)$_2$ (X=8,n=4) and C$_4$(LA)$_2$ (X=10, n=4). For the purpose of comparisons in this same table the same values are indicated for the monocatenary compounds KAM and LAM respectively.

TABLE 1

Physio-chemical and antimicrobial properties of C$_4$(KA)$_2$, (LA)$_2$, KAM and LAM

| Compound | T... mN/cm (25°) | CMC mM (25°) | MIC (μg/ml) | | | | | | |
|---|---|---|---|---|---|---|---|---|---|
| | | | 1 | 2 | 3 | 4 | 5 | 6 | 7 |
| C$_4$(KA)$_2$ | 25 | 7.8 × 10$^{-6}$ | 64 | 32 | 16 | 8 | 8 | 8 | 8 |
| C$_4$(LA)$_2$ | 25 | 4.0 × 10$^{-6}$ | | >128 | | 32 | 32 | 16 | 16 |
| KAM | 30.2 | 14.1 × 10$^{-8}$ | | >128 | | | >128 | | |
| LAM | 30.0 | 3.7 × 10$^{-3}$ | 64 | >128 | 32 | >128 | 64 | 64 | >128 |

1. *Alcaligenes faecalis* ATTCC 8750
2. *Bordeltella bronchiseptica* ATCC
3. *Streptococcus faecalis* ATCC 10541
4. *Bacilus subtilis* ATCC 6633
5. *Staphylococcus aereus* ATCC 25178
6. *Staphylococcus epidermidis* ATCC 155-1
7. *Micrococcus luteus* ATCC 9341

We claim:

1. Cationic geminal surfactants of the type NαNωbis (Nαacyl-arginin) α,ω, diamino alkyl dichlorohydrates as antimicrobial agents with high surface activity, characterized by the general formula:

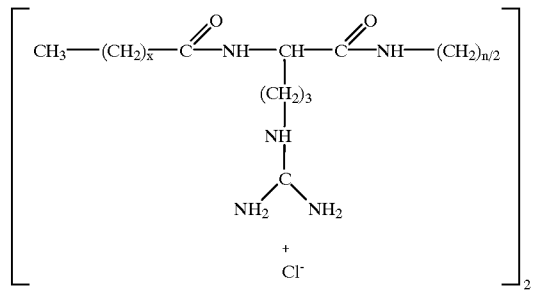

wherein x=8–14 and n=2–8.

2. A process for preparing cationic surfactants with the general formula according to claim 1, characterized by the following steps:

a) forming nitroarginin, using as starting aminoacid, L-arg, D-arg or DL-arg and as protector of the guanidino group of the arginin, the HClnitro group b) forming Nα-acyl-nitroarginin parting from the nitroarginin and fatty acid, using linear fatty acid chlorides of 10–18 atoms as acylants of the nitroarginin in a hydroalcoholic medium c) forming NαNωbis(Nαacyl-nitroarginin)α,ω diaminoalkylamide parting from Nα acyl-nitroarginin and diaminoalkyl, using as condensation agents, such as BOP or DCCD.

d) forming NαNωbis(Nαacyl-arginin)α,ω, diaminoalkylamide dichlorhydrate by means of a catalytic hydrogenation, in PD/C and formic methanolacid with a proportion comprised between 30–50% of NαNωbis (Nαacylnitroarginin)α,ω, diaminoalkyl.

3. A process according to claim 2, characterized in that for step a) the following reaction is carried out: dissolving hydrochloride of L-arginin in concentrated sulphuric acid, with a proportion of 50% (W,V,), eliminating into space, the formed hydrochloric acid; whereafter a quantity of pulverized ammonium nitrate is added to this solution and left to react at least during 15 minutes at room temperature and after removing the gas formed, the mixture is poured on the ground ice and left to cool at 0° C.; and the solution is brought to 6.8 pH by addition of concentrated ammonium and maintained at the temperature of 0° C. until the total precipitation of the product, approximately 48 hours; whereafter the thus formed precipitate, is filtered and crystallized with hot water.

4. A process according to claim 2, characterized in that for step b), a solution is prepared in the range of 0.10–0.30 mole of nitroarginin and Na(OH) in an aqueous solution of 20 to 30% acetone; next, an equimolecular quantity of fatty acid chloride is added slowly, keeping the pH comprised between 11 and 13 by means of the addition of NA(OH), whereafter the mixture is maintained under agitation during various hours and HCl is added until an acid pH is reached, whereby when a white precipitate appears, which is filtered, washed with water and ether, and finally, crystallized in ethanol-ether.

5. A process according to claim 2, characterized in that for step c) a solution is prepared of 0.30–0.50 mol of Nα-acyl-nitroarginin and excess of tertiary organic base (triethylamine or N-methyl morpholine) in chloroform or else, dimethylformamide, whereby the condensing agent BOP is added to the mixture in a concentration comprised between 0.30–0.50 mole and the alkyl diamine in a concentration comprised between 0.15 and 0.25 mol, the reaction mixture being maintained under agitation from 15–30 hours at a temperature comprised between 10 and 25° C., subsequently adding ether, with the appearance of a precipitate which is washed several times with ether.

6. A process according to claim 2, characterized in that step d) is carried out by deprotection of the nitro group for attaining the Nα-acyl-arginin dimers by a catalytic hydrogenation in a medium which contains PD/C and formic methanol-acid in a proportion comprised between 30–50% in formic acid at a pressure of at least 50 atm, room temperature and in a maximum time of 24 hours.

7. Surfactants according to claim 1, characterized by their antimicrobial activity versus agents including, "*Alicaligenes faecalis, Bordeltella bronchiseptica, Streptococcus faecalis, Bacilus subtilis, Staphylococcus aereus, Staphylococcus epidermidis* and *Micrococcus luteus.*

* * * * *